(12) United States Patent
Griffin

(10) Patent No.: US 8,771,325 B2
(45) Date of Patent: Jul. 8, 2014

(54) TAPERED THREADED ORTHOPEDIC FASTENER ENGAGING PREDETERMINED RADIAL PRELOADS

(76) Inventor: T. Hall Griffin, Longview, TX (US)

(*) Notice: Subject to any disclaimer, the term of this patent is extended or adjusted under 35 U.S.C. 154(b) by 574 days.

(21) Appl. No.: 12/902,513

(22) Filed: Oct. 12, 2010

(65) Prior Publication Data
US 2011/0125199 A1    May 26, 2011

Related U.S. Application Data (63) Continuation-in-part of application No. 12/592,235, filed on Nov. 20, 2009, which is a continuation-in-part of application No. 12/592,248, filed on Nov. 20, 2009.

(51) Int. Cl.
A61B 17/04 (2006.01)
A61B 17/86 (2006.01)
A61F 2/08 (2006.01)
A61B 17/60 (2006.01)

(52) U.S. Cl.
CPC ........ *A61B 17/8625* (2013.01); *A61B 17/8635* (2013.01); *A61B 17/60* (2013.01)
USPC .......................................... 606/312; 606/309

(58) Field of Classification Search
USPC ............................. 606/64, 309, 312, 315–317
See application file for complete search history.

(56) References Cited

U.S. PATENT DOCUMENTS

| | | | |
|---|---|---|---|
| 2,532,296 A * | 12/1950 | Giesen | 606/311 |
| 5,242,447 A | 9/1993 | Borzone | |
| 5,593,410 A | 1/1997 | Vrespa | |
| 5,665,087 A | 9/1997 | Huebner | |
| 5,961,524 A | 10/1999 | Crombie | |
| 6,375,657 B1 | 4/2002 | Doubler et al. | |
| 6,565,573 B1 | 5/2003 | Ferrante et al. | |
| 6,689,137 B2 | 2/2004 | Reed | |
| 6,743,233 B1 | 6/2004 | Baldwin et al. | |
| 6,949,100 B1 | 9/2005 | Venturini | |
| 6,953,463 B2 | 10/2005 | West, Jr. | |
| 7,001,389 B1 | 2/2006 | Navarro et al. | |

(Continued)

OTHER PUBLICATIONS

International Search Report and Written Opinion of the International Searching Authority issued in PCT/US2010/056905 and mailed May 30, 2011 and Informal Comments on Written Opinion and International Search Report filed in PCT/US2010/056905 on Aug. 25, 2011.

(Continued)

*Primary Examiner* — Andrew Yang
*Assistant Examiner* — Olivia C Chang
(74) *Attorney, Agent, or Firm* — Zeman-Mullen & Ford, LLP (57) ABSTRACT

An orthopedic fastener rated to be received into a corresponding bone specimen. The corresponding bone specimen has an overall outer thickness from near cortex to far cortex. Preferably, but optionally, the corresponding bone specimen also has a predetermined bone hole preparation which includes a pilot hole through the near cortex and into the far cortex. The fastener itself comprises a plurality of cutting flutes on one end. The cutting flutes transition into a tapered male threaded portion. The tapered male threaded portion provides a plurality of self-tapping threads. The self-tapping threads taper from a minimum thread crest diameter $D_{min}$ proximal to the cutting flutes to a maximum thread crest diameter $D_{max}$ distal from the cutting flutes. The cutting flutes are further rated to ream the pilot hole, when provided, to a diameter of about $D_{min}$.

6 Claims, 6 Drawing Sheets

(56) References Cited

U.S. PATENT DOCUMENTS

| | | | |
|---|---|---|---|
| 7,198,488 | B2 | 4/2007 | Lang et al. |
| 2001/0047175 | A1 | 11/2001 | Doubler et al. |
| 2002/0045897 | A1 | 4/2002 | Dixon et al. |
| 2002/0128657 | A1* | 9/2002 | Hansson ............... 606/73 |
| 2003/0158555 | A1 | 8/2003 | Sanders et al. |
| 2004/0044345 | A1 | 3/2004 | Demoss et al. |
| 2006/0095040 | A1* | 5/2006 | Schlienger et al. ........ 606/73 |
| 2006/0116686 | A1 | 6/2006 | Crozet |
| 2007/0053765 | A1 | 3/2007 | Warnick et al. |
| 2008/0177335 | A1 | 7/2008 | Melkent |
| 2008/0234762 | A1* | 9/2008 | Forstein et al. ........... 606/312 |
| 2010/0168802 | A1 | 7/2010 | Pathak |

OTHER PUBLICATIONS

Timothy L. Biliouris et al.: "The effect of radial preload on the implant-bone interface: a cadaveric study"; Journal of Orthopaedic Trauma, vol. 4, No. 3, pp. 323-332; c 1989.

C. Hyldahl et al:"Induction and prevention of pin loosening in external fixation: an in vivo study on sheep tibiae"; Journ. of Orth. Trauma, vol. 5, No. 4, pp. 485-492; c 1991.

Author Unknown, "The basics of internal fixation" (8 pages), date circa 2005, downloaded from Internet at http://www.rcsed.ac.uk/fellows/Ivanrensburg/classification/commonfiles/basics_of_internal_fixation.htm.

Stratec Medical (aka Synthes), "External Distal Radius Fixator, Supplement to the 8 mm rod fixator system: Surgical technique" (11 pages), date circa 2005, downloaded from Internet at http://www.synthes.com/html/uploads/media/036.000.233.pdf.

Orthofix Limited, "Xcaliber bone screws" brochure (2 pages), date Dec. 2002, downloaded from Internet at http://www.orthofix.com/ftp/assets/Product/Product_Files/XCaliber%20bone%20screw/bone_screws1.pdf.

* cited by examiner

TAPERED THREADED ORTHOPEDIC FASTENER ENGAGING PREDETERMINED RADIAL PRELOADS

RELATED APPLICATIONS

This application is a continuation-in-part of commonly-invented, co-pending U.S. patent application "Limiting Radial Preloads in Securing an Orthopedic Fastener", Ser. No. 12/592,235, filed Nov. 20, 2009. This application is also a continuation-in-part of commonly-invented, co-pending U.S. patent application "Engaging Predetermined Radial Preloads in Securing an Orthopedic Fastener", Ser. No. 12/592,248, also filed Nov. 20, 2009.

FIELD OF THE INVENTION

This invention relates generally to orthopedic fasteners, and more specifically, in preferred embodiments, to orthopedic fasteners having a tapered threaded connection configured to exert predetermined amounts of radial preload into the cortical bone surrounding the fastener's regions of contact with the bone.

BACKGROUND OF THE INVENTION

A common complication of fracture repair, external fixation (or other orthopedic procedures in which fasteners are inserted into bone) is loosening of the fastener over time at the fastener/bone interface. In their article "The Effect of Radial Preload on the Implant/Bone Interface: A Cadaveric Study", Biliouris et al. suggest several reasons for this loosening, including micro-movement of the bone tissue as axial or bending loads are exerted on the fastener during normal use of the fastened bone by the patient after surgery. As described in some detail in the above-referenced article (hereafter referred to as "Biliouris et al."), such axial and bending loads can cause circumferential and other micro-displacement of the fastener as secured into the bone. This micro-displacement temporarily deforms the shape and size of the bone hole into which the fastener is secured, resulting in loss of circumferential contact between the fastener and the bone, which in turn leads to higher stress conditions at the remaining areas of contact. However, while the higher elasticity of the fastener allows the fastener to resume its original shape and relative position within the bone hole after loading, the lower elasticity of the bone surrounding the bone hole leaves the hole potentially damaged after loading. As a result, there is a loss of contact between fastener and the bone during and potentially after loading, resulting in micro-motion between fastener and bone, manifesting itself over time and repetitive loading as loosening of the fastener.

Biliouris et al. also discuss the use of radial preload to counteract loosening of fasteners under repetitive loads in external fixation. The basic concept of radial preload is to "oversize" the diameter of the fastener within the bone hole. In this way, the bone material around the "oversized" portion of the fastener is compressed, tightening the contact between the fastener and the bone material, encouraging intimate and sustained contact during operational loading, and thereby reducing the propensity for loosening.

However, as taught by Biliouris et al., the bone material's comparatively low elasticity limits the amount of radial preload that can be absorbed by the bone material without causing cracking of the bone material around the oversized portion of the fastener. Biliouris et al. observe that a fastener diameter more than about 0.2 mm greater than the receiving bone hole is prone to cause micro-cracking in surrounding cortical bone material.

The reference in this disclosure so far to "bone" deserves further discussion. Orthopedic fasteners are typically designed to fasten either cortical bone or cancellous bone. Cortical bone, typically found on the outside of a bone, is much tougher and harder than cancellous bone, which is typically found on the inside of a bone. Cancellous bone has soft and malleable characteristics, whereas cortical bone is considerably harder. While radial preload is understood to provide advantages in both cortical and cancellous bone, the inventive focus of this disclosure is on the radial preload imparted by fasteners secured in cortical bone.

U.S. Pat. No. 6,949,100 (Venturini) discloses an orthopedic fixation pin with a tapered thread. While Venturini mentions use in the art of radial preload, Venturini's disclosure and invention focuses on thread profile geometry as a way to enhance the fixation pin's grip on bone.

U.S. Pat. No. 5,961,524 (Crombie) discloses an orthopedic fastener with a tapered thread. The fastener is configured to be received into a smooth hole of substantially the same taper as the thread on the fastener. Once secure into the into the hole, the fastener is given a small amount of extra tightening to compress bone material surrounding the threads in order to improve grip of the fastener on the bone. Crombie's disclosure, however, appears to be solving the problem of improving bone-to-fastener contact rather than imparting limited or controlled amounts of radial preload into the bone surrounding the fastener. As a result, no structure to measure or limit radial preload is disclosed.

U.S. Pat. No. 7,198,488 (Lang et al.), U.S. Pat. No. 5,593,410 (Vrespa) and U.S. Pat. No. 6,953,463 (West, Jr.) illustrate fastener thread styles understood to be advantageous in improving fastener grip in either cortical or cancellous bone. These disclosures provide no guidance, however, on imparting limited or controlled amounts of radial preload into the bone surrounding the fastener.

Likewise U.S. Pat. No. 6.565,573 (Ferrante et al.) and U.S. Pat. No. 6,375,657 (Doubler et al.) disclose bone fasteners with generally tapered threads, but the disclosures of these patents provide no guidance on imparting limited or controlled amounts of radial preload into the bone surrounding the fastener.

U.S. Pat. No. 7,001,389 (Navarro et al.) discloses fasteners with various thread configurations, including tapered threads, to assist in securing a plate to bone. As with other prior art discussed above, however, Navarro et al. provide no guidance on imparting limited or controlled amounts of radial preload into the bone surrounding the fastener.

There is therefore a need in the art for an orthopedic fastener specially designed to exert radial preload on the surrounding bone so that the radial preload reduces the likelihood of loosening of the fastener under repetitive loads. Such a new fastener will advantageously engage a predetermined amount of radial preload on cortical bone into which it is received. In preferred applications, such predetermined amounts of radial preload will not exceed about 0.2 mm of radial preload. Such a new fastener may further, or alternatively, advantageously provide structure, in other embodiments, limiting the amount of radial preload imparted into surrounding bone to about 0.2 mm.

SUMMARY OF THE INVENTION

The present invention addresses one or more of the above-described drawbacks of the prior art. One aspect of the invention includes an orthopedic fastener rated to be received into a corresponding bone specimen. The corresponding bone specimen has an overall outer thickness from near cortex to far cortex. Preferably, but optionally, the corresponding bone specimen also has a predetermined bone hole preparation which includes a pilot hole through the near cortex and into the far cortex.

The fastener itself comprises a plurality of cutting flutes on one end. The cutting flutes transition into a tapered male threaded portion. The tapered male threaded portion provides a plurality of self-tapping threads. The self-tapping threads taper from a minimum thread crest diameter $D_{min}$ proximal to the cutting flutes to a maximum thread crest diameter $D_{max}$ distal from the the cutting flutes. The cutting flutes are further rated to ream the pilot hole, when provided, to a diameter of about $D_{min}$.

It will be appreciated from the above summary that fasteners of the present invention are rated for particular predetermined bone specimens into which they are to be received and secured. This "rating" aspect of the fasteners is discussed in more detail near the end of the "Detailed Description" section of this disclosure.

It is therefore a technical advantage of the invention to be able to engage predetermined amounts of radial preload on cortical bone material surrounding an orthopedic fastener secured into a specimen of cortical bone. In one embodiment, once the threads in the tapered threaded portion of the fastener are fully engaged in the bone preparation, further tightenings of the fastener impart radial preload into the surrounding bone tissue as the tapered diameter of the fastener increases. By pre-selecting the minimum and maximum diameters of the taper, predetermined amounts of radial preload may be imparted. Once the maximum diameter of the taper has engaged the bone preparation, further tightenings cause the cylindrical threaded portion of the fastener to engage the bone preparation, so as to maintain radial preload already imparted while the fastener is further drawn through the bone preparation. Advantageously, the fastener may be tightened all the way through the bone so that the cylindrical threaded portion engages the entire bone. The fastener is then held in both near and far cortices with a substantially constant radial preload. Optionally, but advantageously, cutting flutes may also be deployed on the end of the fastener to drill and/or ream out a bone preparation to a diameter suitable to engage the minimum diameter of the tapered threaded portion.

A further technical advantage of the invention is that a comparatively simple bone preparation (such as a smooth-bore pilot hole or guide hole), or even no preparation at all, will enable the fastener, once drawn through the bone preparation, to impart substantially constant predetermined amounts of radial preload across the bone. Threaded engagement may also provide greater bone surface area over which to distribute radial preload.

A further technical advantage of the invention is that by pre-selecting the maximum taper diameter on the tapered threaded portion of the fastener to be no more than about 0.2 mm greater than the minimum taper diameter, a predetermined radial preload of no more than about 0.2 mm may be controllably imparted to hold the fastener in the bone. In this way, deployments of the fastener will be consistent with the findings of Biliouris et al. described above (that radial preloads greater than about 0.2 mm may cause micro-cracking and other damage to cortical bone).

A further technical advantage of the invention is to provide fasteners that are relatively simple to manufacture, and that can be rated to be received into a variety of bone preparations in a variety of bone specimen types and thicknesses.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should be also be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION

Figure 1A:
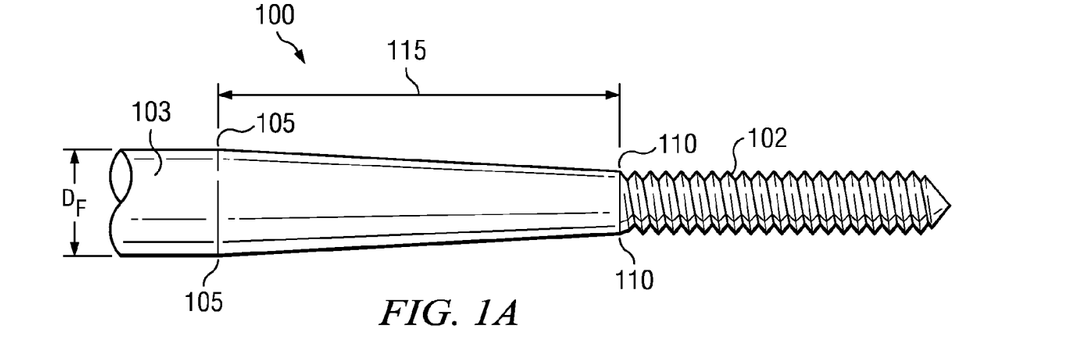
FIGS. 1A, 1B and 1C illustrate, according to a first aspect of the present disclosure, a deployment of fastener 100 into bone specimen 120 through opening 135.
Figure 1B:
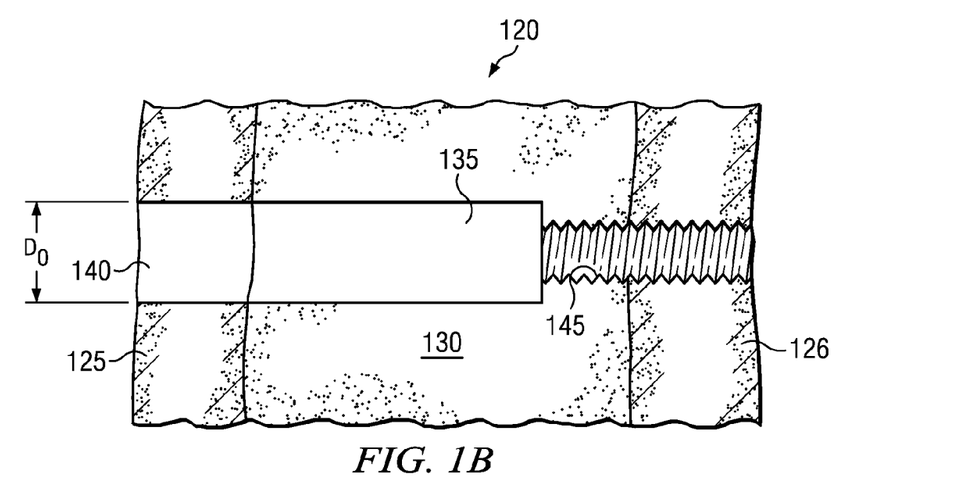
Figure 1C:
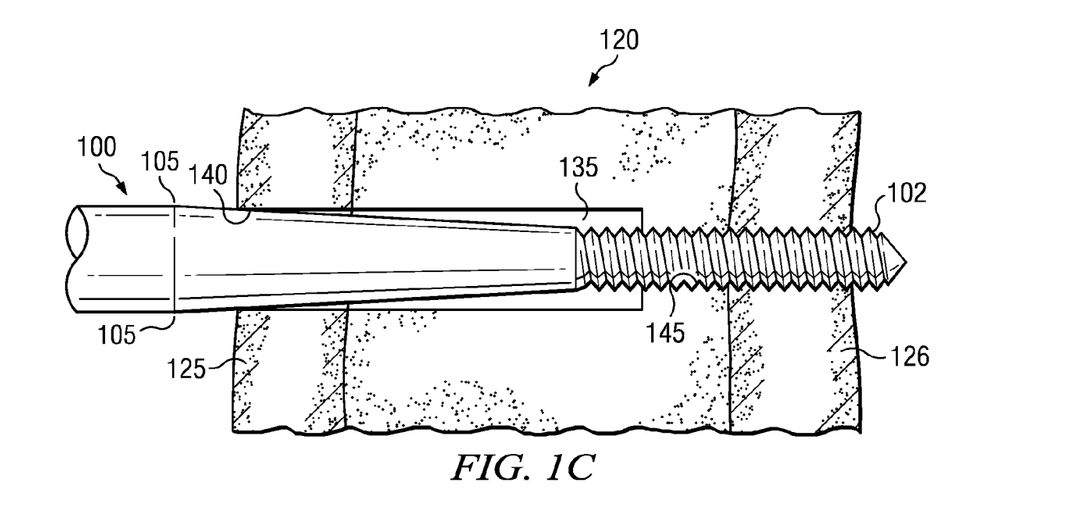

FIGS. 1A, 1B and 1C should be viewed together, and depict a first aspect of the present disclosure, in which an orthopedic fastener 100 is configured to limit and/or control radial preloads exerted in near cortex 125 as fastener 100 is operably secured into bone specimen 120. FIG. 1A illustrates a segment of fastener 100 in isolation. FIG. 1B illustrates bone specimen 120 with opening 135 prepared to receive fastener 100. FIG. 1C illustrates fastener 100 received into opening 135 and operably secured into bone specimen 120.

Referring first to FIG. 1A, fastener 100 provides threaded portion 102 on one end. Fastener 100 further provides unthreaded cylindrical portion 103 with a pre-selected constant diameter $D_F$. Threaded portion 102 and cylindrical portion 103 are separated by a smooth tapered portion 115. Tapered portion 115 is bounded by reference points 105 and 110, as illustrated on FIG. 1A. Reference point 105 is the point at which cylindrical portion 103 ends and tapered portion 115 begins. Reference point 110 is the point at which tapered portion 115 ends. Tapered portion 115 reduces the diameter of fastener 100 from $D_F$, at reference point 105, to a diameter less than $D_F$ at reference point 110. It will be further appreciated that, as described in more detail below with respect to FIG. 1C, the distance on fastener 100 between reference points 105 and 110 is pre-selected.

In the embodiment of fastener 100 depicted in FIG. 1A, threaded portion 102 begins at reference point 110. The invention is not limited in this regard, however. It will be appreciated that in other embodiments (not illustrated), an unthreaded portion may be provided between reference point 110 and threaded portion 102.

Turning now to FIG. 1B, bone specimen 120 is illustrated in cross-section, showing near and far cortices 125, 126 surrounding interior portion 130. It will be appreciated that interior portion 130 may comprise cancellous bone and/or fatty bone marrow. Bone specimen 120 as illustrated on FIG. 1B has been prepared to receive fastener 100 from FIG. 1A. More specifically, opening 135 has been pre-configured to receive fastener 100. Circular entry hole 140 has pre-selected diameter $D_O$, and extends through near cortex 125 into interior portion 130 of bone specimen 120. In the embodiment illustrated in FIG. 1B, opening 135 further provides female threaded section 145 provided through to far cortex 126. The threads on female threaded section 145 are pre-selected to mate with threaded portion 102 on fastener 100 (as shown on FIG. 1A). It will be appreciated that, although not illustrated on FIG. 1B, alternative embodiments will omit female threaded section 145, or provide a small diameter pilot hole in its place suitable to receive self-tapping threads deployed on threaded portion 102. In such alternative embodiments, threaded portion 102 on fastener 100 (as shown on FIG. 1A) will provide self-tapping threads. The inventive material disclosed herein is independent of the manufacturing technique used to provide female threaded section 145 in opening 135.

FIG. 1C shows fastener 100 (as illustrated in isolation on FIG. 1A) received into opening 135 in bone specimen 120 (as illustrated in isolation on FIG. 1B). FIG. 1C shows threaded portion 102 on fastener 100 operably secured into threaded section 145 in opening 135. $D_F$ on fastener 100 is pre-selected to be no more than about 0.2 mm greater than $D_O$ at entry hole 140 in near cortex 125. The length of tapered portion 115 on fastener 100 (as shown on FIG. 1A) is pre-selected to enable fastener 100 (as shown in FIG. 1C) to contact entry hole 140 along the length of tapered portion 115 (shown on FIG. 1A). In this way, as fastener 100 on FIG. 1C is drawn into opening 135 by rotating threaded portion 102 into threaded section 145, reference point 105 is moved closer to entry hole 140, urging $D_O$ on entry hole 140 to enlarge. Accordingly, radial preload is exerted at the interface of entry hole 140 and fastener 100, allowing the advantages of radial preload to benefit the securement of fastener 100 in bone specimen 120. However, in accordance with the invention, as fastener 100 is drawn further into opening 135, and as reference point 105 passes into entry hole 140, since $D_F$ is pre-selected to be no more than about 0.2 mm greater than $D_O$, the maximum amount of radial preload that securement of fastener 100 in bone specimen 120 can exert on entry hole 140 is about 0.2 mm. This value is consistent with the teaching of Biliouris et al., discussed in the background section of this disclosure, finding that about 0.2 mm is generally a maximum amount of radial preload that a specimen of cortical bone can withstand without suffering damage such as micro-cracking.

With further reference to FIGS. 1B and 1C, it will be appreciated that, although not illustrated, other embodiments may provide opening 135 with a profile through near cortex 125 that is shaped other than a cylindrical entry hole such as item 140, as illustrated. For example, the profile of opening 135 through near cortex 125 could be tapered. In such alternative embodiments, it will be understood that $D_O$, as illustrated on FIG. 1B, will be provided as a predetermined minimum entry diameter constricting the profile of opening 135 through near cortex 125.

Figure 2A:
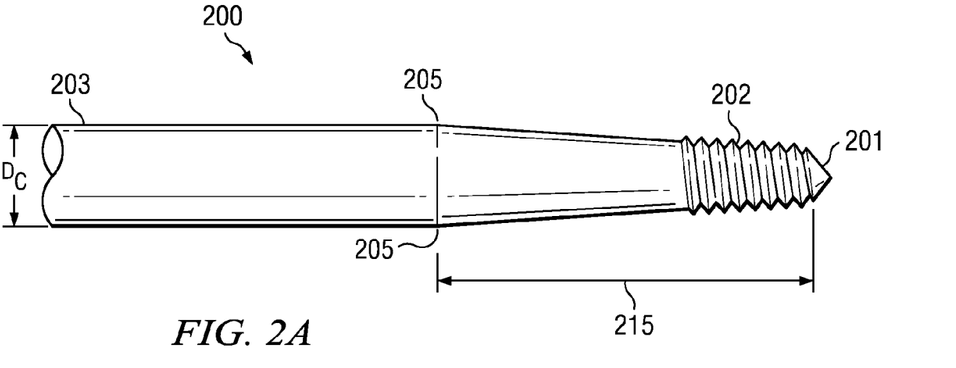
FIGS. 2A, 2B and 2C illustrate, according to a second aspect of the present disclosure, a deployment of fastener 200 into bone specimen 220 through opening 235.
Figure 2B:
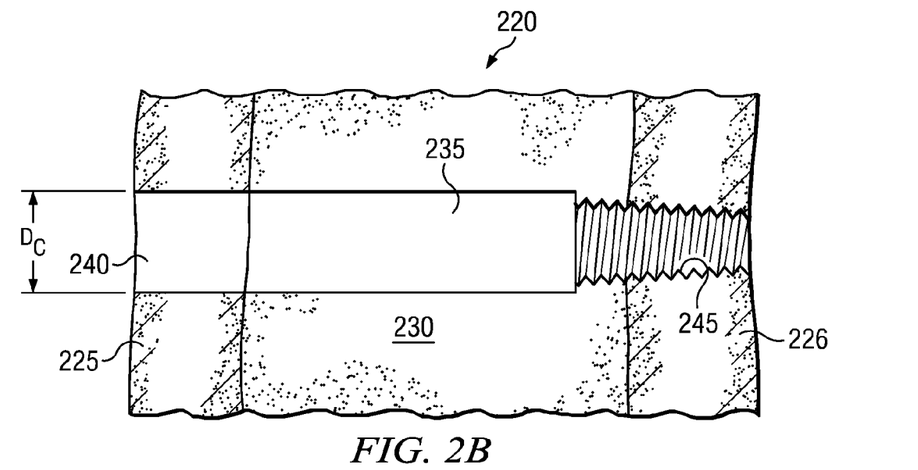
Figure 2C:
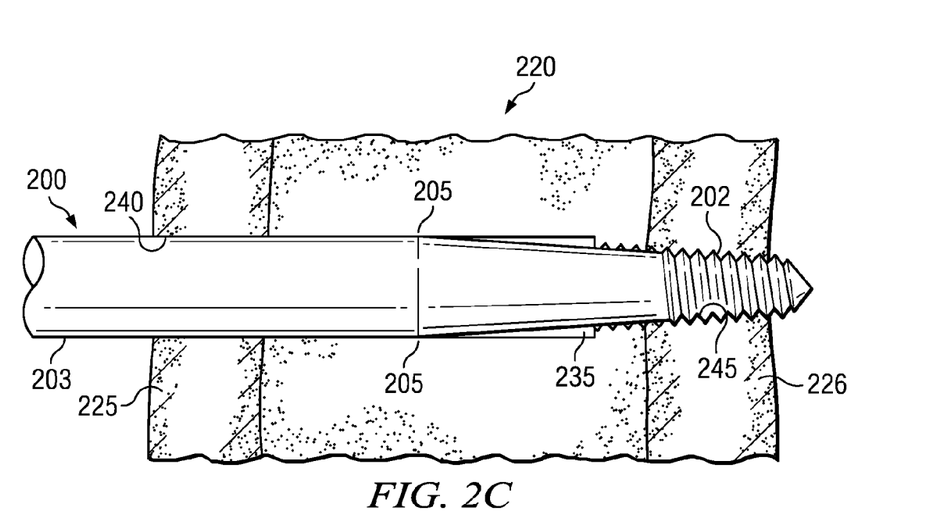

Turning now to FIGS. 2A, 2B and 2C, which should be viewed together, a second aspect of the present disclosure is illustrated, in which an orthopedic fastener 200 is configured to limit and/or control radial preloads exerted in far cortex 226 as fastener 200 is operably secured into bone specimen 220.

Referring first to FIG. 2A, orthopedic fastener 200 provides tapered portion 215 on one end 201 of fastener 200. Fastener 200 further provides unthreaded cylindrical portion 203 adjacent to tapered portion 215. Cylindrical portion 203 is of constant diameter $D_C$. Reference point 205 on fastener 200 is the point at which tapered portion 215 and cylindrical portion 203 transition into one another. As shown on FIG. 2A, threaded portion 202 is deployed on tapered portion 215, at end 201 of fastener 200. FIG. 2A illustrates threaded portion 202 deployed only partially over tapered portion 215. It will be appreciated, however, in other embodiments (not illustrated), threaded portion 202 may deployed over the entire length of tapered portion 215.

The taper profile on tapered portion 215, whether constant or otherwise, is pre-selected. Moreover, as will be described in more detail further on, the dimensional characteristics of the threads on threaded portion 202 (such as diameter, pitch, depth and profile) are also pre-selected.

FIG. 2B illustrates bone specimen 220 in cross-section, showing near and far cortices 225, 226 surrounding interior portion 230. It will be appreciated that interior portion 230 may comprise cancellous bone and/or fatty bone marrow. Bone specimen 220 as illustrated on FIG. 2B has been prepared to receive fastener 200 from FIG. 2A. More specifically, opening 235 has been pre-configured to receive fastener 200. Circular entry hole 240 extends through near cortex 225 into interior portion 230 of bone specimen 220. In the embodiment illustrated in FIG. 2B, the diameter of entry hole 240 is pre-selected to be $D_C$, substantially the same diameter as the diameter of cylindrical portion 203 on fastener 200 (as shown on FIG. 2A). However, as will be discussed in more detail with reference to FIG. 2C, additional embodiments may provide entry hole 240 in bone specimen 220 with diameters or profiles other than $D_C$. The invention is not limited with respect to any particular diameter or profile of entry hole 240 in bone specimen 220.

With continuing reference to FIG. 2B, opening 235 further provides tapered female threaded section 245 provided in far cortex 226, wherein the threads on tapered female threaded section 245 are pre-selected to mate with threaded portion 202 on fastener 200 (as shown on FIG. 2A). In a preferred embodiment, such thread mating advantageously includes mating of thread taper, pitch, depth and profile.

FIG. 2C shows fastener 200 (as illustrated in isolation on FIG. 2A) received into opening 235 in bone specimen 220 (as illustrated in isolation on FIG. 2B). FIG. 2C shows threaded portion 202 on fastener 200 operably secured into threaded section 245 in opening 235. As noted immediately above in the discussion of FIG. 2B, the threads on threaded portion 202 on fastener 200 are pre-selected to mate with the threads on threaded section 245 in opening 235 in bone specimen 220. In this way, as fastener 200 on FIG. 2C is threadably engaged into opening 235, the taper on the interface between threaded portion 202 and threaded section 245 causes threads of increasingly larger diameter on threaded portion 202 to engage threaded section 245 in bone specimen 220. As a result, as fastener 200 on FIG. 2C is threadably engaged into opening 235, radial preload is imparted into the area of far cortex 226 immediately surrounding threaded section 245.

It will be appreciated that the inventive material disclosed herein is independent of the manufacturing method by which threaded section 245 is provided in opening 235. Threaded section 245 may be provided by any suitable technique, such as, without limitation, self-drilling, pre-drilling and reaming, or step-drilling, with subsequent tapping as required.

Since the thread characteristics of threaded portion 202 and threaded section 245 are pre-selected, a pre-desired amount of radial preload can be imparted into far cortex 226. Conventional methods may be used to measure, calculate or predict the amount of radial preload being imparted. For example, conventional algorithms or tables may be used to determine how many turns of fastener 200 will impart a pre-desired amount of radial preload. Alternatively, a conventional torque wrench may be used to tighten fastener 200, where pre-calibration (such as via a look-up table) will dictate how much torque imparted on fastener 200 is equivalent to a pre-determined desired amount of radial preload.

Figure 4A:
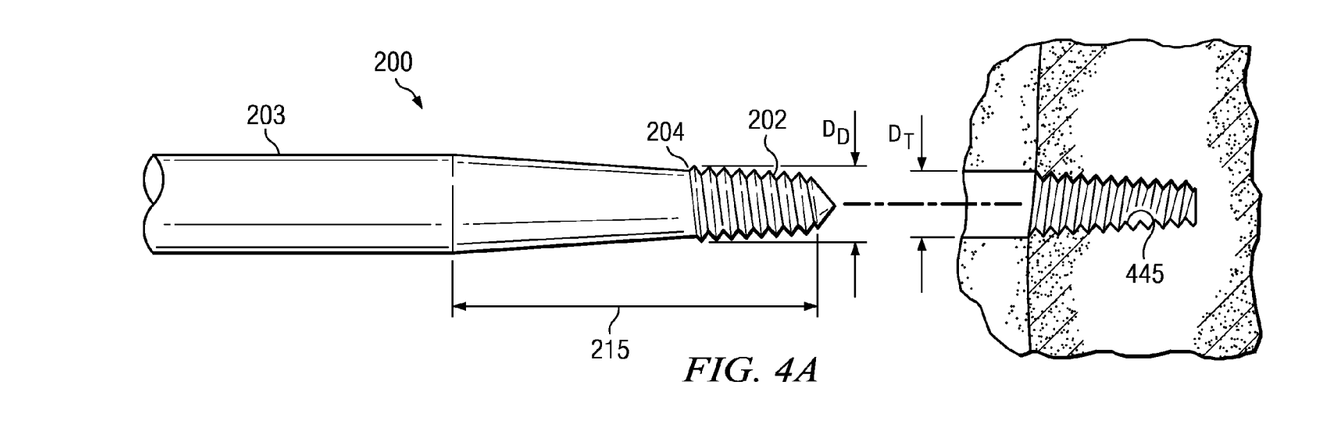
FIGS. 4A, 4B and 4C illustrate exemplary embodiments of structure that may be deployed on fasteners of the present invention to limit the maximum radial preload available to be imparted in "mating tapered thread" configurations described herein.
Figure 4B:
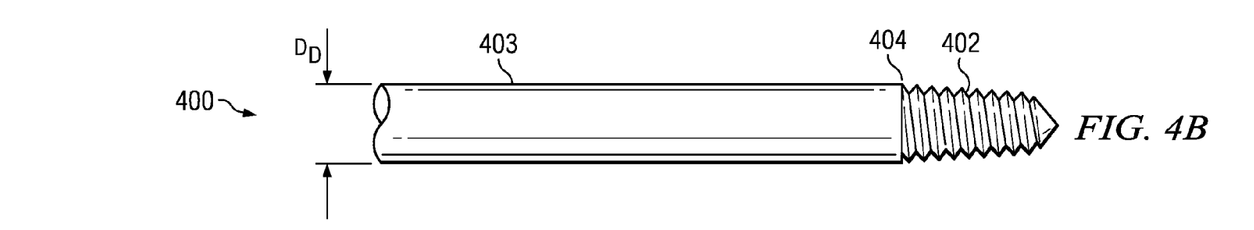
Figure 4C:
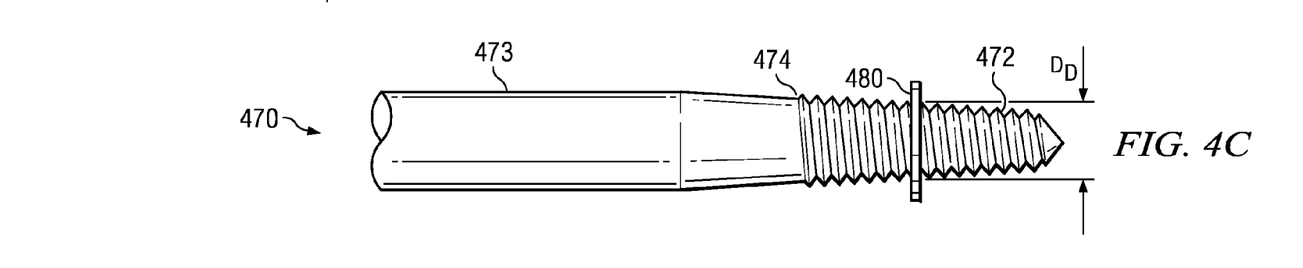

Alternatively, embodiments of fastener 200 may be provided to limit the maximum radial preload available to be imparted by further tightening fastener 200 once threaded portion 202 and threaded section 245 are threadably engaged. FIGS. 4A to 4C illustrate exemplary embodiments of structure configured to limit the maximum radial preload available to be imparted in such "mating tapered thread" configurations. It will be appreciated, however, that the inventive material disclosed herein is not limited to any particular structure provided to limit radial preload once threaded portion 202 and threaded section 245 are threadably engaged, if indeed any such structure to limit radial preload is provided at all.

FIG. 4A shows, as also illustrated on FIG. 2A, fastener 200 providing threaded portion 202 on tapered portion 215. In the embodiment illustrated in FIG. 4A, however, unthreaded portion 203 on fastener 200 is identified, as well as discontinuity 204. It will be appreciated that unthreaded portion 203 transitions into threaded portion 202 at discontinuity 204. FIG. 4A also identifies $D_D$ on fastener 200, the diameter along tapered portion 215 at which discontinuity 204 is provided.

FIG. 4A also shows tapered female threaded section 445 disposed to receive threaded portion 202 on fastener 200. It will be appreciated that in the embodiments for limiting "mating tapered thread" radial preload described with reference to FIGS. 4A to 4C, bone preparations such as threaded section 445 on FIG. 4A, disposed to receive threaded portion 202 on fastener 200, may be located in either near or far cortices of a bone specimen. The location of bone preparations such as threaded section 445 on FIG. 4A is independent of the inventive material disclosed herein describing structure configured to limit the maximum radial preload available to be imparted in "mating tapered thread" configurations.

Referring again to FIG. 4A, and analogous to threaded portion 202 and threaded section 245 as described above with reference to FIG. 2C, the threads on threaded portion 202 on FIG. 4A are pre-selected to mate with the threads on threaded section 445. Again analogous to threaded portion 202 and threaded section 245 on FIG. 2C, since the thread characteristics of threaded portion 202 on FIG. 4A and threaded section 445 are pre-selected, a pre-desired amount of radial preload can be imparted into the bone material surrounding threaded section 445 by threadably engaging threaded portion 202 on threaded section 445 and then further tightening. However, in the embodiment illustrated on FIG. 4A, threaded section 445 provides diameter $D_T$ at its widest opening (i.e., its entryway), and $D_D$ on fastener 200 and $D_T$ on threaded section 445 are pre-selected so that $D_D$ is no more than about 0.2 mm greater than $D_T$.

Now, with continued reference to FIG. 4A, it will be understood that as threaded portion 202 is threadably engaged on threaded section 445 and further tightened, discontinuity 204 on fastener 200 will act as a "stop" to prevent further tightening of fastener 200 into threaded section 445 once discontinuity 204 reaches the first thread on threaded section 445. Since $D_D$ on fastener 200 and $D_T$ on threaded section 445 are pre-selected so that $D_D$ is no more than about 0.2 mm greater than $D_T$, the maximum radial preload available to be imparted into the bone material surrounding threaded section 445 is no more than about 0.2 mm.

It will be readily appreciated that, within the scope of the embodiment illustrated in FIG. 4A, $D_D$ and $D_T$ can also be pre-selected to have different relative values, so as to limit the maximum radial preload available to be imparted to amounts other than about 0.2 mm. However, as taught by Biliouris et al., $D_D$ and $D_T$ in the embodiment illustrated in FIG. 4A should preferably be configured to limit the maximum radial preload available to about 0.2 mm in order to avoid cause micro-cracking and other damage to the cortical bone.

Further to FIG. 4A and the accompanying disclosure immediately above, FIG. 4B illustrates another embodiment of structure configured to limit the maximum radial preload available to be imparted in "mating tapered thread" configurations. Fastener 400 in FIG. 4B is similar to fastener 200 in FIGS. 2A and 4A, except that discontinuity 404 separates tapered threaded portion 402 and cylindrical unthreaded portion 403. Threaded portion 402 on fastener 400 on FIG. 4B is, however, inventively the same in all respects as threaded portion 202 on FIG. 4A, with $D_D$ identified as the diameter at discontinuity 404. In the embodiment of FIG. 4B, however, $D_D$ on threaded portion 402 is the same as the cylindrical diameter of unthreaded portion 403. It will be appreciated that in some applications, the embodiment illustrated in FIG. 4B may be more convenient to manufacture, by cutting threaded portion 402 onto a cylindrical profile with a pre-selected diameter of $D_D$. In such embodiments, it will be understood to be important to establish discontinuity 404 at the transition from unthreaded portion 403 to threaded portion 402 via, for example, a thread profile transition effective to prevent further tightening of fastener 400 once the thread(s) at $D_D$ on threaded portion 402 engage the thread(s) at $D_T$ on threaded section 445 (as illustrated on FIG. 4A).

Further to FIGS. 4A and 4B, and the corresponding accompanying disclosure immediately above, FIG. 4C illustrates yet another embodiment of structure configured to limit the maximum radial preload available to be imparted in "mating tapered thread" configurations. Fastener 470 in FIG. 4C is similar to fastener 200 in FIGS. 2A and 4A, except that discontinuity 474 separates tapered threaded portion 472 and tapered unthreaded portion 473 at a point of larger diameter than is desired to be pre-selected as $D_D$. Stop 480 is provided instead on threaded portion 472 at pre-selected diameter $D_D$. It will be appreciated that with the exception of stop 480, rather than discontinuity 474, being provided on threaded portion 472 to define $D_D$, threaded portion 472 on fastener 470 on FIG. 4C is, however, inventively the same in all respects as threaded portion 202 on FIG. 4A. In this way, if fastener 470 on FIG. 4C is threadably engaged on threaded section 445 on FIG. 4A and further tightened, stop 480 will prevent further tightening of fastener 470 into threaded section 445 once stop 480 reaches the first thread on threaded section 445.

Stop 480 on fastener 470 is illustrated on FIG. 4C as a washer. The inventive material disclosed herein is not limited in this regard, however. Stop 480 may be any structure on threaded portion 472 suitable to define $D_D$ and to prevent further tightening past $D_D$. Other examples might include a lip or the head of a screw or bolt.

With reference back now to FIG. 2C, it will be appreciated that when fastener 200 is threadably engaged into opening 235 so as to impart radial preload in far cortex 226, care should be taken so as not to exceed about 0.2 mm of radial preload. As taught by Biliouris et al., and discussed above, amounts of radial preload in excess of about 0.2 mm have been shown to cause micro-cracking and other damage to the cortical bone. Consideration should be given to deploying structure on fastener 200, such as, without limitation, structure from among the examples suggested above with reference to FIGS. 4A to 4C, in order to limit the maximum radial preload available to be imparted by "mating tapered thread" configurations to about 0.2 mm. It will be appreciated, however, that any such structure to limit radial preload imparted by mating tapered threads is optional within the scope of the inventive material disclosed herein.

As shown on FIGS. 2A and 2B, and discussed briefly above, the illustrated embodiment in FIGS. 2A, 2B and 2C provide cylindrical portion 203 on fastener 200 with substantially the same diameter $D_C$ as entry hole 240 on bone specimen 220. It will be readily appreciated, however, that in other embodiments (not illustrated) entry hole 240 may be provided with a diameter less than $D_C$. In this way, when fastener 200 is introduced into opening 235 on bone specimen 220, and cylindrical portion 203 is pressed into entry hole 240, radial preload may be imparted into near cortex 225.

Again, care should be exercised when providing an entry hole 240 on bone specimen 220 with diameter less than $D_C$, in order not to impart more than about 0.2 mm of radial preload when cylindrical portion 203 is pressed into entry hole 240. As taught by Biliouris et al., and as discussed above, radial preloads exceeding about 0.2 mm may damage near cortex 225. Indeed, it will be appreciated that further embodiments of fastener 200 (not illustrated) may provide an arrangement on near cortex 225 similar to those illustrated on FIG. 1C, in which a limited amount of radial preload is imparted when cylindrical portion 203 is pressed into a reduced-diameter entry hole 240. In these embodiments, tapered portion 215 (as shown on FIG. 2A) may be of a pre-selected length so that, when introduced into opening 235 on bone specimen 220 (as shown on FIG. 2C), reference points 205 are now located in near cortex bone 225, or outside of bone specimen 220 completely. The diameter of entry hole 240 in bone specimen 220 in these embodiments is pre-selected to be no smaller than about 0.2 mm less than $D_C$. By analogy to FIG. 1C and its accompanying disclosure above, such alternative (but not illustrated) embodiments will allow radial preload in near cortex 225 to be limited to no more than about 0.2 mm.

With further reference to FIGS. 2B and 2C, it will be appreciated that, although not illustrated, other embodiments may provide opening 235 with a profile through near cortex 225 that is shaped other than a cylindrical entry hole such as item 240, as illustrated. For example, the profile of opening 235 through near cortex 225 could be tapered. In such alternative embodiments, it will be understood that $D_C$, as illustrated on FIG. 2B, will be provided as a predetermined minimum entry diameter constricting the profile of opening 235 through near cortex 225.

Figure 3A:
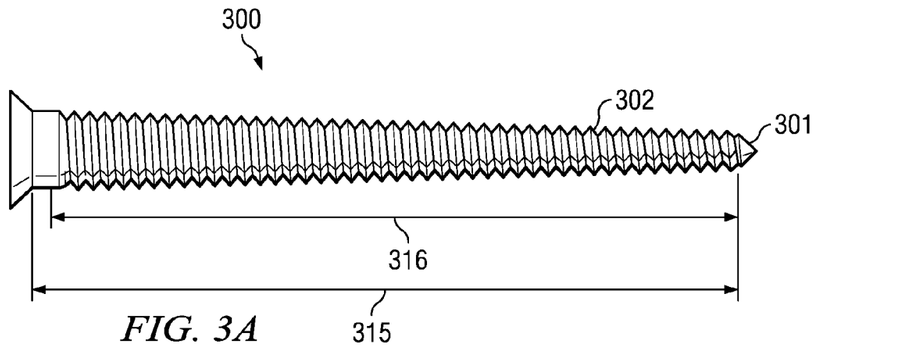
FIGS. 3A, 3B and 3C illustrate, according to a third aspect of the present disclosure, a deployment of fastener 300 into bone specimen 320 through opening 335.
Figure 3B:
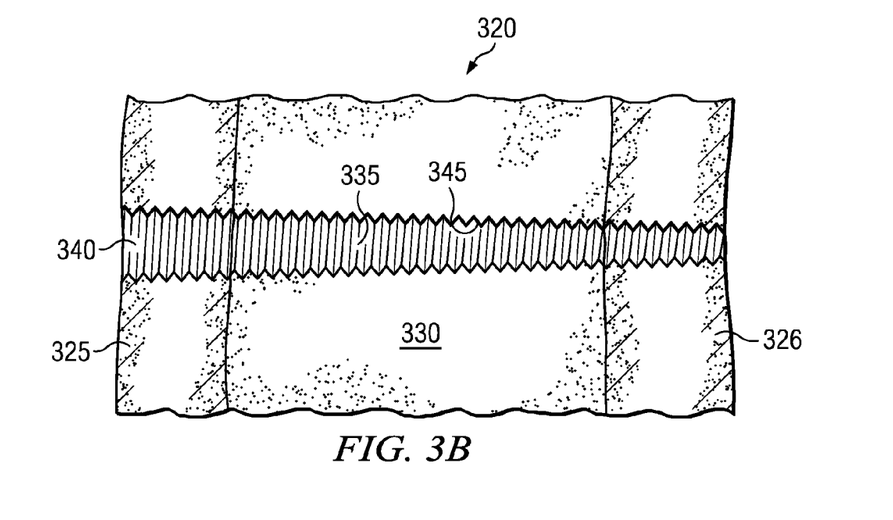
Figure 3C:
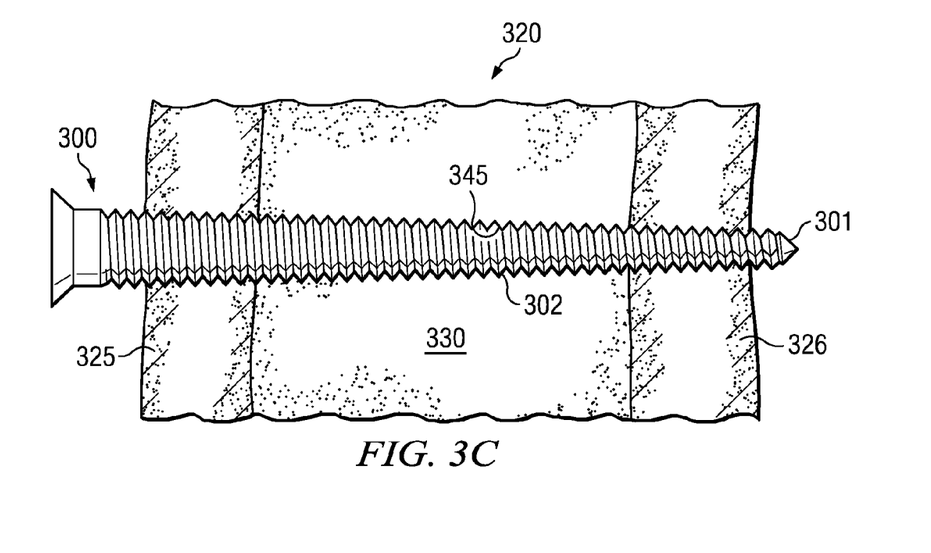

Turning now to FIGS. 3A, 3B and 3C, which should be viewed together, a third aspect of the present disclosure is illustrated, in which an orthopedic fastener 300 is configured to limit and/or control radial preloads exerted in both near cortex 325 and far cortex 326 as fastener 300 is operably secured into bone specimen 320. For general reference, subject to the detailed disclosure that follows, fastener 300, as shown operably secured in bone specimen 320 on FIG. 3C, limits and/or controls radial preloads in both near and far cortices 325 and 326 in functionally the same way as fastener 200 limits and/or controls radial preloads in far cortex 226 on FIG. 2C, as described above.

With reference first to FIG. 3A, orthopedic fastener 300 provides tapered portion 315 on one end 301 of fastener 300. Although the invention is not limited in this regard, FIG. 3A shows tapered portion 315 comprising substantially the entire length of fastener 300. Other embodiments (not illustrated) may provide fastener 300 with additional length via, for example, a cylindrical portion provided distal from end 301 and tapered portion 315, and/or a cylindrical portion appended to end 301.

FIG. 3A further illustrates threaded portion 302 provided on tapered portion 315, at end 301 of fastener 300. Threaded portion 302 is deployed over threaded portion length 316. FIG. 3A illustrates threaded portion length 316 deployed substantially over the entire length of tapered portion 315. It will be appreciated, however, in other embodiments (not illustrated, but discussed below with reference to FIG. 3C), threaded portion length 316 may deployed at end 301 of fastener 300 but over only part of tapered portion 315.

The taper profile on tapered portion 315, whether constant or otherwise, is pre-selected. Further, threaded portion length 316 is also pre-selected. Moreover, as will be described in more detail further on, the dimensional characteristics of the threads on threaded portion 302 (such as diameter, pitch, depth and profile) are also pre-selected.

FIG. 3B illustrates bone specimen 320 in cross-section, showing near and far cortices 325, 326 surrounding interior portion 330. It will be appreciated that interior portion 330 may comprise cancellous bone and/or fatty bone marrow. Bone specimen 320 as illustrated on FIG. 3B has been prepared to receive fastener 300 from FIG. 3A. More specifically, opening 335 has been pre-configured to receive fastener 300. Opening 335 begins at entry 340, and provides tapered female threaded section 345 through near cortex 325, interior portion 330, and far cortex 326. The threads on tapered female threaded section 345 are pre-selected to mate with threaded portion 302 on fastener 300 (as shown on FIG. 3A). In a preferred embodiment, such thread mating advantageously includes mating of thread taper, pitch, depth and profile.

Analogous to the disclosure above describing FIGS. 2B and 2C, it will be appreciated on FIGS. 3B and 3C that the inventive material disclosed herein is independent of the manufacturing method by which female threaded section 345 is provided in bone specimen 320. Threaded section 345 may be provided by any suitable technique, such as, without limitation, self-drilling, pre-drilling and reaming, or step-drilling, with subsequent tapping as required.

FIG. 3C shows fastener 300 (as illustrated in isolation on FIG. 3A) received into opening 335 in bone specimen 320 (as illustrated in isolation on FIG. 3B). FIG. 3C shows threaded portion 302 on fastener 300 operably secured into threaded section 345 in opening 335. Note that notation of opening 335 has been omitted from FIG. 3C for clarity, but may be identified via reference to FIG. 3B.

It will be appreciated from FIG. 3C that threaded portion length 316 on fastener 300 (as shown on FIG. 3A) is pre-selected to enable threaded portion 302 on fastener 300 (as shown on FIG. 3C) to engage threaded section 345 on bone specimen 320 in both near cortex 325 and far cortex 326. Moreover, as noted immediately above in the discussion of FIG. 3B, the threads on threaded portion 302 on fastener 300 are pre-selected to mate with the threads on threaded section 345 in opening 335 in bone specimen 320. In this way, as fastener 300 on FIG. 3C is threadably engaged into opening 335, the taper on the interface between threaded portion 302 and threaded section 345 causes threads of increasingly larger diameter on threaded portion 302 to engage threaded section 345 in bone specimen 320.

As a result, as fastener 300 on FIG. 3C is threadably engaged into opening 335, radial preload is imparted into the areas of near cortex 325, interior portion 330 and far cortex 326 immediately surrounding threaded section 345. As noted above, this mechanism to impart radial preload is functionally the same as the manner in which fastener 200 limits and/or controls radial preloads in far cortex 226 on FIG. 2C. It will be understood, however, that although fastener 300 on FIG. 3C is capable of imparting radial preload into interior portion 330 as well as near and far cortices 325 and 326, any radial preload operably retained in interior portion 330 is not of inventive significance to this disclosure. While such radial preload retained in interior portion 330, if any, may be of some practical assistance preventing loosening of fastener 300 under operating loads, the inventive focus of this disclosure is on radial preload imparted by fastener 300 on near and far cortices 325 and 326.

With further reference to FIG. 3C, since the thread characteristics of threaded portion 302 and threaded section 345 are pre-selected, a pre-desired amount of radial preload can be imparted into near cortex 325 and far cortex 326. Conventional methods may be used to measure, calculate or predict the amount of radial preload being imparted. For example, conventional algorithms or tables may be used to determine how many turns of fastener 300 will impart a pre-desired amount of radial preload. Alternatively, a conventional torque wrench may be used to tighten fastener 300, where pre-calibration (such as via a look-up table) will dictate how much torque imparted on fastener 300 is equivalent to a pre-determined desired amount of radial preload.

It will be recalled from earlier disclosure herein that FIGS. 4A to 4C illustrate exemplary embodiments of structure configured to limit the maximum radial preload available to be imparted in "mating tapered thread" configurations, such as have just been described with reference to FIGS. 3A to 3C. It will be understood that any of the embodiments illustrated, disclosed or suggested above with respect to FIGS. 4A to 4C may be deployed on fastener 300 as illustrated and described with reference to FIGS. 3A to 3C. It will be further understood that any of the embodiments illustrated, disclosed or suggested above with respect to FIGS. 4A to 4C may be deployed on fastener 300 so as to limit the maximum radial preload available to be imparted in the near cortex only, in the far cortex only, or concurrently in both cortices. It will also be appreciated, however, that the inventive material disclosed herein is not limited to any particular structure provided to limit the maximum radial preload available to be imparted by fastener 300, if indeed any such structure to limit radial preload is provided at all in either cortex.

With reference back now to FIG. 3C, it will be appreciated that when fastener 300 is threadably engaged into opening 335 so as to impart radial preload in near cortex 325 and far cortex 326, care should be taken so as not to exceed about 0.2 mm of radial preload. As taught by Biliouris et al., and discussed above, amounts of radial preload in excess of about 0.2 mm have been shown to cause micro-cracking and other damage to the cortical bone. Consideration should be given to deploying structure on fastener 300, such as, without limitation, structure from among the examples suggested above with reference to FIGS. 4A to 4C, in order to limit the maximum radial preload available to be imparted by "mating tapered thread" configurations to about 0.2 mm. As noted above, however, it will be appreciated that any such structure to limit radial preload imparted by mating tapered threads is optional within the scope of the inventive material disclosed herein.

Figure 5A:
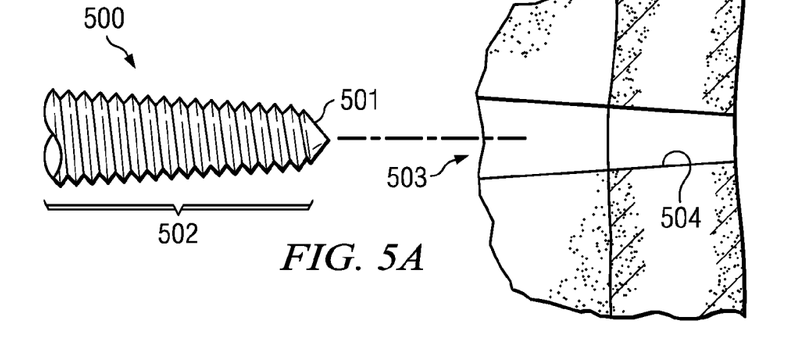
FIGS. 5A, 5B and 5C illustrate, according to additional aspects of the present disclosure, deployments of fastener 500 with male tapered threaded portion 502 into alternative bone preparations 503, 513 and 523 respectively.
Figure 5B:
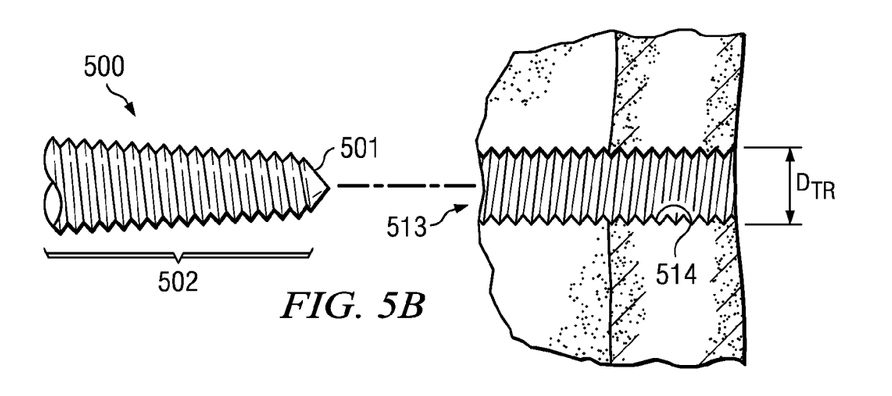
Figure 5C:
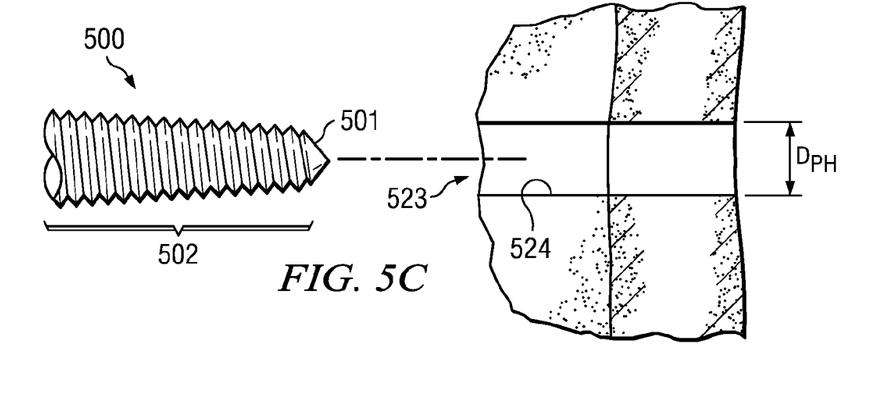

Turning now to FIGS. 5A through 5C, further embodiments are illustrated wherein a fastener having threads of pre-determined taper (such as fastener 300 on FIG. 3A) may be deployed in additional types of bone preparations so as to impart radial preload when the fastener is tightened. An exemplary deployment in which the fastener and the receiving bone preparation have "matching tapered threads" has been described in detail above with reference to FIGS. 3A, 3B and 3C. It will be understood, however, that scope of the inventive material disclosed herein is not confined to such a "matching tapered threads" deployment, and indeed is not limited to any particular bone preparation into which a fastener with tapered threads may be received.

For example, FIG. 5A illustrates a deployment in which an orthopedic fastener 500 has a male tapered threaded portion 502 on one end 501. In the example of FIG. 5A, fastener 500 is to be received into bone preparation 503, comprising unthreaded tapered portion 504. In an exemplary but preferred embodiment of FIG. 5A, the threads on male tapered threaded portion 502 are self-tapping threads, and the taper on male tapered threaded portion 502 is rated to match the taper on unthreaded tapered portion 504.

It will be appreciated that, although not illustrated, "self-tapping threads", as discussed with respect to male tapered threaded portion 502 in the preceding paragraph, may refer throughout this disclosure to self-tapping threads with or without a leading series of "tapping flutes". Some embodiments may provide, with equivalent enabling effect, a series of tapping flutes leading the self-tapping threads to prepare the bone tissue surrounding the self-tapping threads to receive self-tapping engagement. The provision or omission of such tapping flutes is not considered of inventive significance to this disclosure, and thus distinction will not be made in the discussion of "self-tapping threads", notwithstanding that tapping flutes may or may not be provided in any specific embodiment.

Turning now to FIG. 5B, orthopedic fastener 500 is again illustrated having a male tapered threaded portion 502 on one end 501. In the example of FIG. 5B, however, fastener 500 is to be received into bone preparation 513, comprising female cylindrical threaded portion 514 having a pre-selected thread root diameter $D_{TR}$. In an exemplary but preferred embodiment of FIG. 5B, the taper on male tapered threaded portion 502 is rated to provide (1) a tapering range of thread crest diameters that includes $D_{TR}$, and (2), ideally, tapering threads having a thread profile that matches the thread profile of the threads on female cylindrical threaded portion 514.

With reference now to FIG. 5C, orthopedic fastener 500 is once more illustrated having a male tapered threaded portion 502 on one end 501. In the example of FIG. 5C, however, fastener 500 is to be received into bone preparation 523, comprising cylindrical pilot hole 524 having a pre-selected diameter $D_{PH}$. In an exemplary but preferred embodiment of FIG. 5C, the threads on male tapered threaded portion 502 are self-tapping threads, and the taper on male tapered threaded portion 502 is rated to provide a tapering range of thread root diameters that includes $D_{PH}$. In another exemplary embodiment (not illustrated), it will be appreciated that if $D_{PH}$ is too small as drilled to receive the threads on male tapered threaded portion 502, cutting flutes may be provided on end 501 of fastener 500 in order to ream out $D_{PH}$ to a diameter suitable to receive the self-tapping threads on male tapered threaded portion 501 on fastener 500.

While the embodiments of FIGS. 5A, 5B and 5C have been described above with reference to bone preparations 503, 513 and 523, it will be further appreciated that in other embodiments (not illustrated), bone preparations 503, 513 or 523 may not be necessary. Specifically, when cutting flutes (not illustrated) are provided on end 501 of fastener 500, and are of the type capable of self-drilling a hole in bone tissue, and then reaming the self-drilled hole to a pre-determined diameter, it will be seen that fastener 500 may be engaged into bone tissue without any specific prior bone preparation.

For the avoidance of doubt, cutting flutes as described in the preceding paragraph are distinguished from "tapping flutes" as described earlier with respect to self-tapping threads on male tapered threaded portion 502 on FIG. 5A. For purposes of this disclosure, cutting flutes, when provided, will self-drill and/or ream an opening in bone tissue to a predetermined diameter. In contrast, tapping flutes, when provided, will cut initial threads in bone tissue being prepared to receive self-tapping threads.

At this point it will be once again appreciated that the scope of the inventive material disclosed herein is not limited to any particular deployment of bone preparation in which tapered male threads on an orthopedic fastener may be received. For example, the exemplary bone preparations disclosed herein, such as with reference to FIGS. 3A to 3C, or with reference to 5A to 5C, may be deployed in any combination in either the near cortex or the far cortex, or both. Further, when cutting flutes are provided and are of the type capable of self-drilling, no bone preparation may be necessary.

It will be recalled from earlier disclosure herein that FIGS. 4A to 4C illustrate exemplary embodiments of structure configured to limit the maximum radial preload available to be imparted in "mating tapered thread" configurations, such as have been described above with reference to FIGS. 3A to 3C. It will be understood that any of the embodiments illustrated, disclosed or suggested above with respect to FIGS. 4A to 4C may also be deployed on fastener 500 as illustrated and described with reference to FIGS. 5A to 5C. It will be further understood that any of the embodiments illustrated, disclosed or suggested above with respect to FIGS. 4A to 4C may be deployed on fastener 500 so as to limit the maximum radial preload available to be imparted in the near cortex only, in the far cortex only, or concurrently in both cortices. It will also be appreciated, however, that the inventive material disclosed herein is not limited to any particular structure provided to limit the maximum radial preload available to be imparted by fastener 500, if indeed any such structure to limit radial preload is provided at all in either cortex.

However, as taught by Biliouris et al., and as discussed above, amounts of radial preload in excess of about 0.2 mm have been shown to cause micro-cracking and other damage to the cortical bone. Advantageously, therefore, consideration should be given to deploying structure on fastener 500, such as, without limitation, structure from among the examples suggested above with reference to FIGS. 4A to 4C, in order to limit the maximum radial preload available to be imparted to about 0.2 mm. As noted above, however, it will be appreciated that any such structure to limit radial preload is optional within the scope of the inventive material disclosed herein.

Figure 6A:
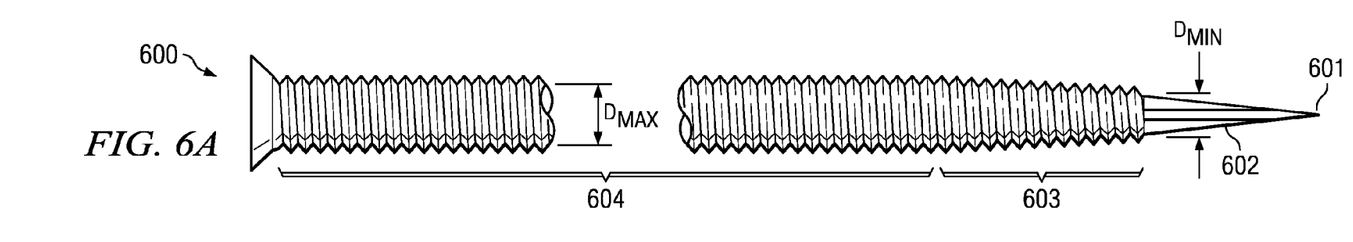
FIGS. 6A, 6B and 6C illustrate, according to a further aspect of the present disclosure, a deployment of fastener 600 into bone specimen 620 through opening 635.
Figure 6B:
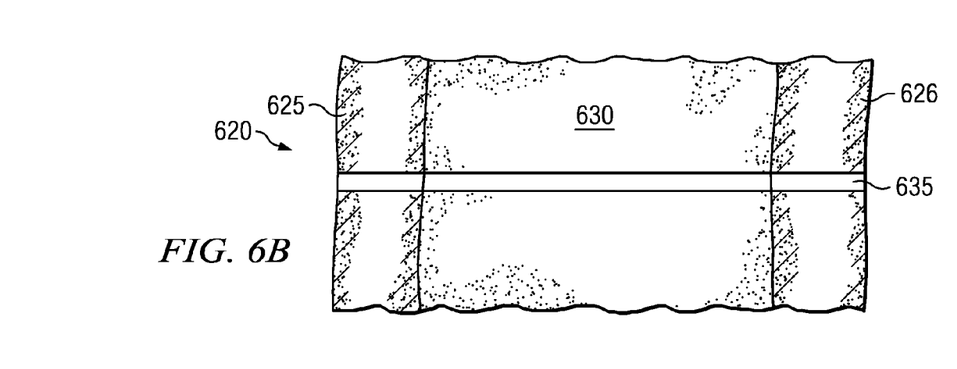
Figure 6C:
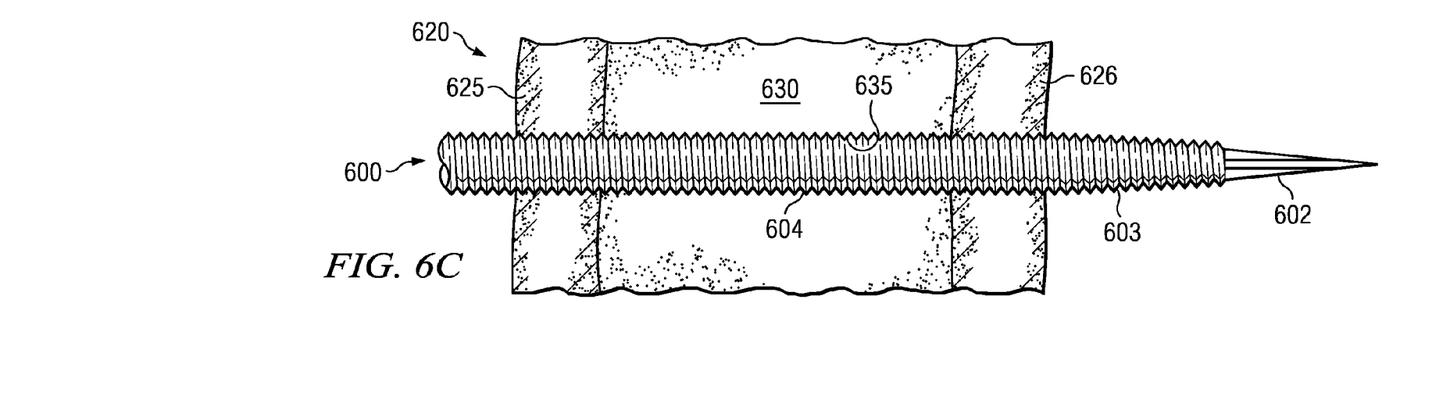

FIGS. 6A, 6B and 6C illustrate a further variation of the deployment illustrated in FIG. 5C. Consistent within the broader scope of the inventive material disclosed herein, the embodiment of FIGS. 6A, 6B and 6C provides a substantially constant predetermined radial preload over a predetermined length of bone tissue. The predetermined length of bone tissue may include either the near cortex or the far cortex, or preferably both (as illustrated in FIGS. 6B and 6C). The embodiment of FIGS. 6A, 6B and 6C has a further technical advantage in that it provides a relatively simple bone preparation into which the orthopedic fastener of FIG. 6A may be received and deployed quickly and accurately.

FIG. 6A illustrates orthopedic fastener 600 having cutting flutes 602 on one end 601. Cutting flutes 602 transition into male tapered threaded portion 603 on fastener 600. Male tapered threaded portion 603 in turn transitions into male cylindrical threaded portion 604. Male tapered threaded portion 603 and male cylindrical threaded portion 604 provide a continuous length of self-tapping threads. Ideally, the length of male cylindrical threaded portion 604 on fastener 600 is rated to be at least as long as a corresponding length of bone tissue over which radial preload is desired to be imparted.

Male tapered threaded portion 603 on FIG. 6A provides a tapering range of thread root diameters, ranging from $D_{MIN}$ as a smallest thread root diameter located next to cutting flutes 602, up to $D_{MAX}$ as a largest thread root diameter. It will be seen on FIG. 6A that male cylindrical threaded portion 604 provides threads of constant thread root diameter $D_{MAX}$. Cutting flutes 602 on FIG. 6A are provided to ream out the diameter of a pilot hole or guide hole to about $D_{MIN}$, so that the self-tapping threads at the $D_{MIN}$ end of male tapered threaded portion 603 may engage the interior surface of the freshly-reamed pilot hole or guide hole. For the avoidance of doubt, cutting flutes 602 on FIG. 6A are distinguished from "tapping flutes" as described earlier with respect to self-tapping threads on male tapered threaded portion 502 on FIG. 5A. For purposes of this disclosure, cutting flutes, when provided, will self-drill or ream an opening in bone tissue to a predetermined diameter. In contrast, tapping flutes, when provided, will cut initial threads in bone tissue being prepared to receive self-tapping threads.

FIG. 6B illustrates bone specimen 620 in cross-section, showing near and far cortices 625, 626 surrounding interior portion 630. It will be appreciated that interior portion 630 may comprise cancellous bone and/or fatty bone marrow. Bone specimen 620 as illustrated on FIG. 6B has been prepared to receive fastener 600 from FIG. 6A. More specifically, opening 635 on FIG. 6B has been pre-configured to receive fastener 600. Opening 635 comprises a simple smooth-bored cylindrical pilot hole (or guide hole) with a diameter advantageously equal to or smaller than $D_{MIN}$ (as illustrated on fastener 600 in FIG. 6A).

FIG. 6C illustrates fastener 600 from FIG. 6A received into opening 635 in bone specimen 620 (as illustrated on FIG. 6B). It will be appreciated from FIG. 6C that as fastener 600 has been received into opening 635 and then screw-tightened until male cylindrical threaded portion 604 is contacting both near and far cortices 625, 626 and interior portion 630. It will be further appreciated from FIG. 6C that as fastener 600 is screw-tightened into opening 635, cutting flutes 602 first ream out the diameter of opening 635 to about $D_{MIN}$. Self-tapping threads on male tapered threaded portion 603 then engage opening 635. As tapered threads of increasingly larger diameter on male tapered threaded portion 603 come to engage opening 635, increasing amounts of radial preload are imparted into the surrounding bone tissue. Eventually, as threads of $D_{MAX}$ diameter start to engage opening 635, male cylindrical threaded portion 604 is now being drawn into opening 635. Continued screw-tightening of fastener 600 enables male cylindrical threaded portion 604 to be drawn through both near and far cortices 625, 626 and interior portion 630.

With further reference now to FIG. 6C, it will be understood that a substantially constant radial preload of ($D_{MAX}$−$D_{MIN}$) has been imparted through the entire bone specimen

620 by drawing male cylindrical threaded portion 604 all the way through opening 635. By pre-selection of $D_{MAX}$, $D_{MIN}$, and the length of male cylindrical threaded portion 604, therefore, orthopedic fastener 600 on FIG. 6A can be rated to impart predetermined amounts of substantially constant radial preload across a corresponding bone specimen of predetermined outer thickness from near cortex to far cortex.

It will be recalled from earlier discussion of Biliouris et al., amounts of radial preload in excess of about 0.2 mm have been shown to cause micro-cracking and other damage to the cortical bone. Thus, in an exemplary but preferred embodiment of orthopedic fastener 600 on FIG. 6A, $D_{MAX}$ and $D_{MIN}$ are advantageously pre-selected so that $D_{MAX}$ is no more than about 0.2 mm more than $D_{MIN}$.

While the embodiment of FIGS. 6A, 6B and 6C has been described above with reference to opening 635 provided in bone specimen 620, it will be further appreciated that in other embodiments (not illustrated), opening 635 may not be necessary. Specifically, when cutting flutes 602 on fastener 600 are of the type capable of self-drilling a hole in bone specimen 620, and then reaming the self-drilled hole to a diameter of about $D_{MIN}$, it will be seen that fastener 600 may be engaged into bone specimen 620 without any specific prior bone preparation.

It was mentioned above in reference to FIG. 3A that, although not illustrated, additional length could be provided to fastener 300 via, for example, a cylindrical portion provided distal from end 301 and/or a cylindrical portion appended to end 301. With reference now to FIG. 3C, it will be appreciated that such additional length is not of inventive significance to this disclosure. Additional length, distal from end 301 and threaded portion length 316, may be provided to fastener 300 by any structural means, so long as threaded portion length 316 (as shown on FIG. 3A) is pre-selected to permit threaded portion 302 on fastener 300 (as shown on FIG. 3C) to engage threaded section 345 in both near cortex 325 and far cortex 326. In similar fashion, additional length may be provided to fastener 500 in the embodiments illustrated in FIGS. 5A, 5B and 5C by any structural means, so long as male tapered threaded portion 502 has sufficient length to engage the portions of bone tissue in which radial preload is desired to be imparted. Moreover, it will be appreciated that additional length may be provided to fastener 600 in the embodiment illustrated in FIGS. 6A, 6B and 6C by any structural means, so long as male cylindrical threaded portion 604 has sufficient length to engage opening 635 all the way through bone specimen 620.

Throughout this disclosure so far, embodiments of fasteners have been described with structural features that may be pre-selected to match corresponding features of bone openings into which they may be received. It will be further appreciated, however, that the converse is true without departing from the spirit and scope of the inventive material disclosed herein. More specifically, with particular reference to FIGS. 1C, 2C and 3C, it will be appreciated that fasteners according to this disclosure may be manufactured as "rated" to be received in corresponding bone hole preparations. It will be understood that when a fastener is rated to be received in a corresponding bone hole preparation, the fastener is manufactured with accompanying disclosure from the manufacturer regarding specific characteristics of a corresponding bone hole preparation that will engage the inventive functionality of the fastener.

For example, in the embodiments disclosed in FIGS. 1A, 1B and 1C, fastener 100 may be manufactured as rated to be received in a corresponding bone hole preparation comprising: (1) a diameter $D_O$ of entry hole 140 that is pre-selected to be smaller than $D_F$ of cylindrical portion 103 on fastener 100, but no more than about 0.2 mm smaller than $D_F$; and (2) an overall thickness of bone specimen 120 that is pre-selected to be in a range of thicknesses that permit tapered portion 115 on fastener 100 to contact entry hole 140 when threaded portion 102 is threadably engaged in far cortex 126.

Similarly, by way of further example in the embodiments disclosed in FIGS. 2A, 2B and 2C, fastener 200 may be manufactured as rated to be received in a corresponding bone hole preparation comprising: (1) a diameter $D_C$ of entry hole 240 that is pre-selected to be substantially the same as $D_C$, the diameter of cylindrical portion 203 on fastener 200, but in no circumstances more than about 0.2 mm smaller than $D_C$; and (2) a threaded section 245 provided in far cortex 226 that is pre-selected to mate with threaded portion 202 on fastener 200 for taper, thread pitch, thread depth and thread profile.

Similarly, by way of further example in the embodiments disclosed in FIGS. 3A, 3B and 3C, fastener 300 may be manufactured as rated to be received in a corresponding bone hole preparation comprising: (1) a threaded section 345 provided in near cortex 325 through to far cortex 326 that is pre-selected to mate with threaded portion 302 on fastener 300 for taper, thread pitch, thread depth and thread profile; and (2) an overall thickness of bone specimen 320 that is pre-selected to be in a range of thicknesses that permit threaded portion length 316 on fastener 300 to engage threaded section 345 in both near cortex 325 and far cortex 326.

Similarly, by way of further example in the embodiments disclosed in FIGS. 5A, 5B and 5C, fastener 500 may be manufactured as rated to be received in a bone hole preparation comprising a fastener thread contact zone pre-selected to threadably engage the fastener, where the fastener thread contact zone includes: (1) an unthreaded tapered portion 504 such that the threads on male tapered threaded portion 502 are self-tapping threads, and the taper on male tapered threaded portion 502 matches the taper on unthreaded tapered portion 504; or (2) a female cylindrical threaded portion 514 having a pre-selected thread root diameter $D_{TR}$, such that the taper on male tapered threaded portion 502 provides a tapering range of thread crest diameters that includes $D_{TR}$, and, ideally, tapering threads having a thread profile that matches the thread profile of the threads on female cylindrical threaded portion 514; or (3) an unthreaded cylindrical portion 524 of diameter $D_{PH}$, such that the threads on male tapered threaded portion 502 are self-tapping threads, and the taper on male tapered threaded portion 502 provides a tapering range of thread root diameters that includes $D_{PH}$.

Similarly, by way of further example in the embodiments disclosed in FIGS. 6A, 6B and 6C, fastener 600 may be manufactured as rated to be received into a bone specimen having (1) an overall outer thickness from near cortex 625 to far cortex 626 that is shorter in length than cylindrical threaded portion 604 on fastener 600, and (2) a predetermined bone hole preparation including a pilot hole (such as opening 635) through the near cortex 625 and into the far cortex 626, where the diameter of the pilot hole may be less than $D_{MIN}$ on tapered threaded portion 603 on fastener 600.

Embodiments of the invention have been described herein with reference to orthopedic fixation pins. It will be appreciated, however, that the invention is not limited in this regard, and that it may be embodied on any orthopedic fastener, such as, without limitation, pedicle screws, orthopedic nails, bone screws, hip screws, or even dental implants.

Those of ordinary skill in this art will further appreciate that the invention is not limited to any particular size of orthopedic fastener.

Although the present invention and its advantages have been described in detail, it should be understood that various changes, substitutions and alternations can be made herein without departing from the spirit and scope of the invention as defined by the appended claims.

I claim:

1. A method for engaging radial preload in securing an orthopedic fastener into a corresponding bone specimen, the method comprising the steps of:
   (A) selecting and preparing the corresponding bone specimen to have an overall outer thickness from near cortex to far cortex;
   (B) providing a fastener, the fastener comprising a plurality of cutting flutes on one end, the cutting flutes disposed to drill and ream a pilot hole to a diameter of about $D_{min}$, the cutting flutes transitioning into a tapered male threaded portion, the tapered male threaded portion providing a plurality of self-tapping threads, the self-tapping threads tapering from a minimum thread crest diameter $D_{min}$ proximal to the cutting flutes to a maximum thread crest diameter $D_{max}$ distal from the cutting flutes, wherein $D_{max}$ is not greater than about 0.2mm more than $D_{min}$, the tapered male threaded portion, at an end distal from the cutting flutes, transitioning into a cylindrical male threaded portion of thread crest diameter $D_{max}$, the cylindrical male threaded portion having substantially the same thread profile as the tapered male threaded portion, the cylindrical male threaded portion extending along the fastener for a length at least as long as the overall outer thickness of the bone specimen; and
   (C) securing the fastener into the bone specimen, so that the cutting flutes drill and ream a pilot hole to a diameter of about $D_{min}$, further tightening of the fastener causing the tapered male threaded portion to follow the cutting flutes into the pilot hole and impart radial preload into surrounding bone tissue, the radial preload reaching a maximum of $D_{max}$ as the cylindrical male threaded portion follows the tapered male threaded portion into the pilot hole.

2. The method of claim 1, in which step (A) further comprises pre-drilling a pilot hole through the near cortex and into the far cortex.

3. A method for engaging radial preload in securing an orthopedic fastener into a corresponding bone specimen, the method comprising the steps of:
   (A) selecting and preparing the corresponding bone specimen to have an overall outer thickness from near cortex to far cortex;
   (B) providing a fastener, the fastener comprising a plurality of cutting flutes on one end, the cutting flutes disposed to drill and ream a pilot hole to a diameter of about $D_{min}$, the cutting flutes transitioning into a tapered male threaded portion, the tapered male threaded portion providing a plurality of self-tapping threads, the self-tapping threads tapering from a minimum thread crest diameter $D_{min}$ proximal to the cutting flutes to a maximum thread crest diameter $D_{max}$ distal from the cutting flutes; and
   (C) securing the fastener into the bone specimen, so that the cutting flutes drill and ream a pilot hole to a diameter of about $D_{min}$, further tightening of the fastener causing the tapered male threaded portion to follow the cutting flutes into the pilot hole and impart radial preload into surrounding bone tissue, the radial preload reaching a maximum of $D_{max}$ as the entire tapered male threaded portion follows the cutting flutes into the pilot hole.

4. The method of claim 3, in which step (A) further comprises pre-drilling a pilot hole through the near cortex and into the far cortex.

5. The method of claim 3, in which $D_{max}$ is not greater than about 0.2 mm more than $D_{min}$.

6. The method of claim 3, in which:
   the tapered male threaded portion on the fastener, at an end distal from the cutting flutes, transitions into a cylindrical male threaded portion of thread crest diameter $D_{max}$, the cylindrical male threaded portion having substantially the same thread profile as the tapered male threaded portion;
   the cylindrical male threaded portion extends along the fastener for a cylindrical thread portion length; and
   the cylindrical portion thread length is at least as long as the overall outer thickness of the bone specimen.

* * * * *